(12) United States Patent
Helmer et al.

(10) Patent No.: US 11,033,688 B2
(45) Date of Patent: Jun. 15, 2021

(54) INJECTION DEVICE WITH AXIALLY MOVING NEEDLE HOLDER

(71) Applicant: Sanofi-Aventis Deutschland GMBH, Frankfurt am Main (DE)

(72) Inventors: Michael Helmer, Frankfurt am Main (DE); Marc Schader, Frankfurt am Main (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 582 days.

(21) Appl. No.: 15/778,494

(22) PCT Filed: Nov. 21, 2016

(86) PCT No.: PCT/EP2016/078277
§ 371 (c)(1),
(2) Date: May 23, 2018

(87) PCT Pub. No.: WO2017/089287
PCT Pub. Date: Jun. 1, 2017

(65) Prior Publication Data
US 2018/0353696 A1 Dec. 13, 2018

(30) Foreign Application Priority Data
Nov. 27, 2015 (EP) .................................. 15196714

(51) Int. Cl.
*A61M 5/24* (2006.01)
*A61M 5/32* (2006.01)
(52) U.S. Cl.
CPC ............ *A61M 5/2466* (2013.01); *A61M 5/24* (2013.01); *A61M 5/3202* (2013.01);
(Continued)

(58) Field of Classification Search
CPC .... A61M 5/2466; A61M 5/24; A61M 5/3202; A61M 5/3293; A61M 2005/2474; A61M 2207/00
See application file for complete search history.

(56) References Cited

U.S. PATENT DOCUMENTS

| 4,231,368 A | 11/1980 | Becker |
| 2004/0044310 A1 | 3/2004 | Suzuki |

(Continued)

FOREIGN PATENT DOCUMENTS

| CN | 1350470 | 5/2002 |
| CN | 101264360 | 9/2008 |

(Continued)

OTHER PUBLICATIONS

PCT International Preliminary Report on Patentability in International Appln. No. PCT/EP2016/078277, dated May 29, 2018, 7 pages.

(Continued)

*Primary Examiner* — Nathan R Price
*Assistant Examiner* — John A Doubrava
(74) *Attorney, Agent, or Firm* — Fish & Richardson P.C.

(57) ABSTRACT

An injection device comprises a housing containing a cartridge, a needle holder including an injection needle, and a cap. The cap is removably engaged with the housing. The injection device also comprises a translating mechanism configured such that linear distal movement of the cap causes proximal movement of the needle holder such that the injection needle pierces the cartridge.

16 Claims, 4 Drawing Sheets

(52) U.S. Cl.
 CPC ... *A61M 5/3293* (2013.01); *A61M 2005/2474* (2013.01); *A61M 2207/00* (2013.01)

(56) References Cited

U.S. PATENT DOCUMENTS

| | | |
|---|---|---|
| 2008/0228147 A1 | 9/2008 | David-Hegerich et al. |
| 2018/0353693 A1* | 12/2018 | Wendland ............ A61M 5/3202 |
| 2018/0353708 A1* | 12/2018 | Schader .................. A61M 5/20 |
| 2018/0361069 A1* | 12/2018 | Schader .............. A61M 5/3202 |

FOREIGN PATENT DOCUMENTS

| | | |
|---|---|---|
| CN | 104284689 | 1/2015 |
| CN | 104321093 | 1/2015 |
| JP | 2003-093506 | 4/2003 |
| JP | 2013-521083 | 6/2013 |
| WO | WO 2000/069488 | 11/2000 |
| WO | WO 2011/110465 | 9/2011 |
| WO | WO 2013/148270 | 10/2013 |
| WO | WO 2013/186617 | 12/2013 |
| WO | WO 2015/140262 | 9/2015 |

OTHER PUBLICATIONS

PCT International Search Report and Written Opinion in International Appln. No. PCT/EP2016/078277, dated Feb. 13, 2017, 9 pages.

* cited by examiner

INJECTION DEVICE WITH AXIALLY MOVING NEEDLE HOLDER

CROSS REFERENCE TO RELATED APPLICATIONS

This application is a U.S. national stage application under 35 USC § 371 of International Application No. PCT/EP2016/078277, filed on Nov. 21, 2016, which claims priority to European Application No. 15196714.8, filed on Nov. 27, 2015, the entire contents of which are incorporated herein by reference.

TECHNICAL FIELD

The present disclosure relates to an injection device.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

Some of the injection devices operate with a cartridge-based injection system. This type of system is typically provided with a separate cartridge pre-filled with medicament and a separate needle sealed in a sterilized packaging. Before injection, the user has to unpack and assemble the packaged needle with the cartridge, i.e. place the cartridge in a cartridge holder within the housing of the device, unseal the packaging containing the needle, and position the needle in the housing of the device. This may be considered time-consuming by some users.

Moreover, some injection devices that include pre-filled cartridges are often stored for a relatively long time before being effectively used for injection.

SUMMARY

An injection device is provided comprising: a housing containing a cartridge; a needle holder including an injection needle; a cap that is removably engaged with the housing; and a translating mechanism configured such that linear distal movement of the cap causes proximal movement of the needle holder such that the injection needle pierces the cartridge.

The translating mechanism may comprise a gear assembly, the gear assembly comprising a first rotary gear, a first linear gear, and a second linear gear.

The cartridge may comprise a pierceable septum, and wherein the injection needle is arranged to pierce the pierceable septum when the needle holder is urged against the cartridge.

The injection device may further comprise a cartridge holder configured to contain the cartridge, and wherein the first rotary gear is rotatably mounted at a distal end of the cartridge holder between the needle holder and the removable cap, the first rotary gear being arranged to mesh with the first linear gear and the second linear gear.

The injection device may further comprise a second rotary gear rotatably mounted at the distal end of the cartridge holder between the needle holder and the removable cap, at a position circumferentially opposite to the first rotary gear, wherein the second rotary gear is arranged to mesh with the first linear gear and the second linear gear.

The first linear gear may be arranged on an outer surface of the needle holder.

The second linear gear may be arranged on an inner surface of the cap.

The cap may further comprise an inner cap portion, wherein the second linear gear is positioned on an inner surface of the inner cap portion.

The injection device may further comprise a needle shield fixed attached at the cap, wherein the needle shield is configured to cover the needle when the cap is engaged with the housing.

The cartridge may contain a medicament.

The injection device may be an auto-injector.

According to another aspect, there is provided a method of coupling a cartridge and a needle holder including an injection needle within an injection device, the method comprising: converting distal movement of a removable cap into proximal movement of the needle holder via a translating mechanism, such that the injection needle pierces the cartridge.

Converting distal movement of the removable cap into proximal movement of the needle holder may comprise meshing a first linear gear at the removable cap with a first rotary gear at the housing and causing the first rotary gear to mesh with a second linear gear at the needle holder such that the needle holder moves proximally towards the cartridge.

The injection device may reduce clogging of the needle by the medicament by preventing contact between the medicament and the needle of the cartridge prior to use. This may reduce delays in the delivery of medicament during the injection. Also, other negative impacts on the medicament when the medicament is in contact with the needle for a long period of storage time, may be reduced.

These and other aspects will be apparent from and elucidated with reference to the embodiments described hereinafter.

BRIEF DESCRIPTION OF THE FIGURES

Exemplary embodiments of the present invention are described with reference to the accompanying drawings, in which.

Reference will now be made in detail to the embodiments, examples of which are illustrated in the accompanying drawings, wherein like reference numerals refer to like elements throughout.

DETAILS DESCRIPTION OF THE FIGURES

An injection device with a translating mechanism for piercing a cartridge contained therein is provided. The injection device comprises a housing containing a cartridge; a needle holder including an injection needle; a cap that is removably engaged with the housing; and a translating mechanism configured such that linear distal movement of the cap causes proximal movement the needle holder such that the injection needle pierces the cartridge. By using this particular translating mechanism configuration, the need for manual unpacking and assembling of the injection needle with the cartridge can be eliminated.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
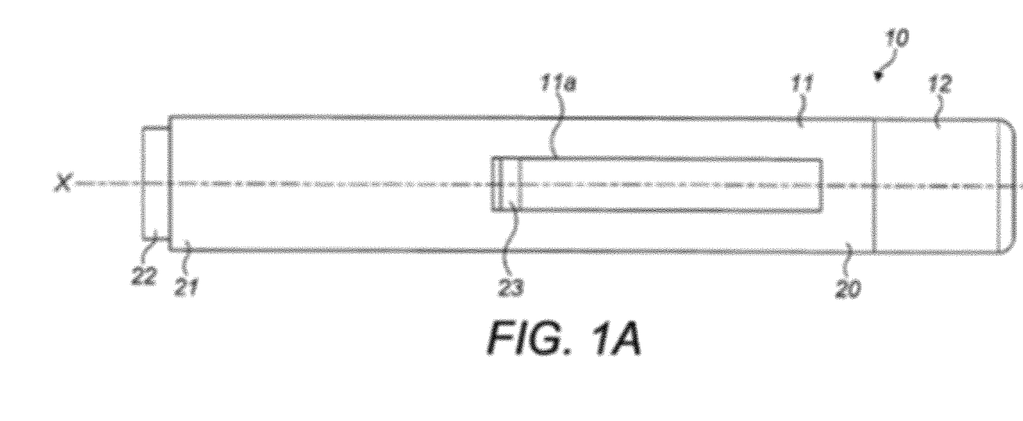
FIGS. 1A and 1B are side-on views of an injection device according to an embodiment.
Figure 1B:
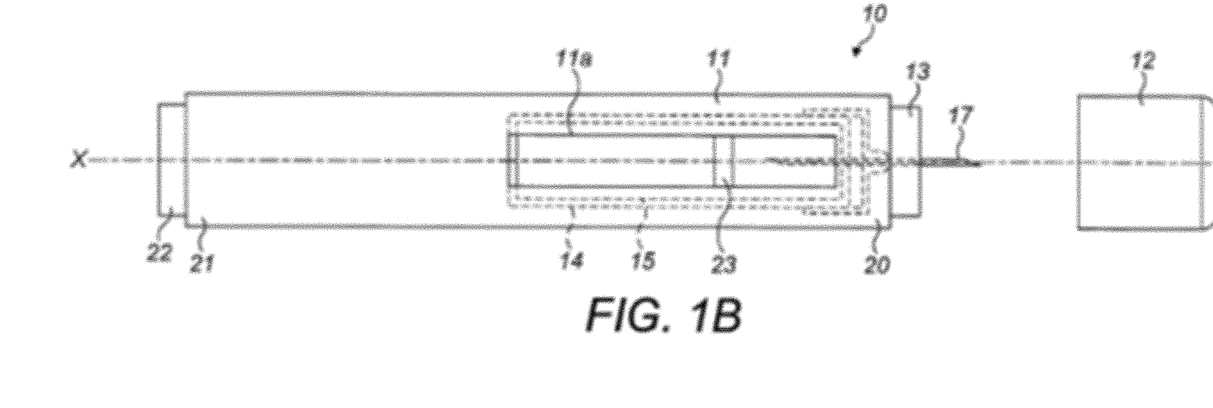

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2A:
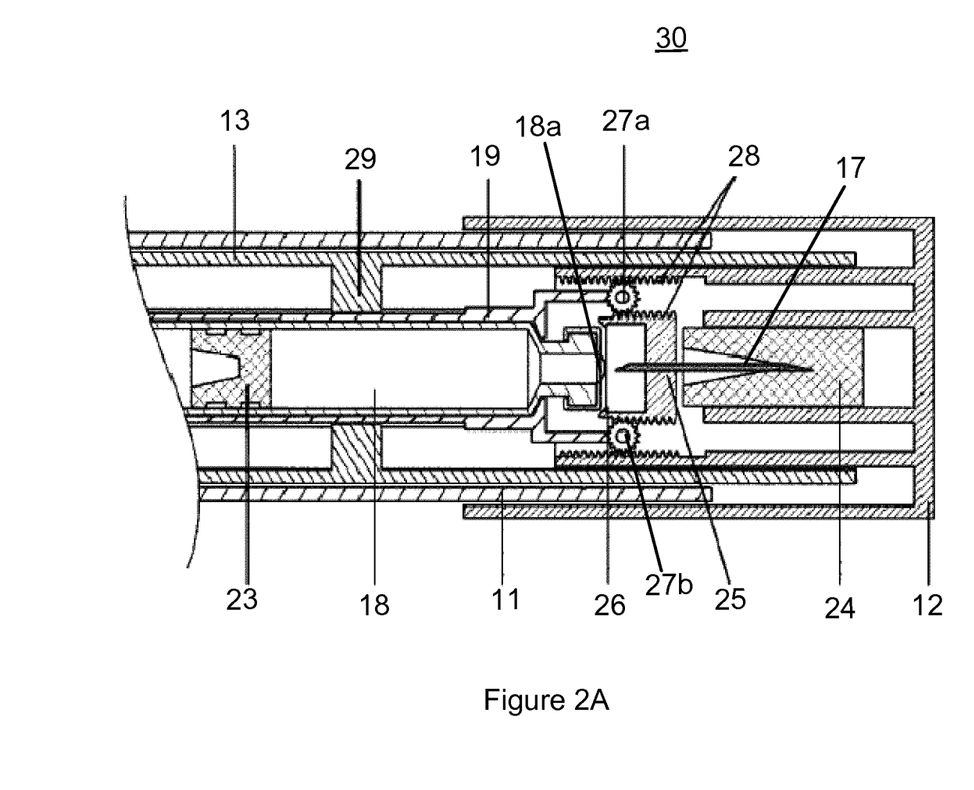
FIG. 2A is a schematic cross-sectional view of part of an injection device in an initial state, according to a first embodiment.

FIG. 2A is a schematic cross-sectional view of part of an injection device in an initial state, according to a first embodiment.

FIG. 2A shows a part of an injector device 30 comprising a housing 11. A cartridge holder 19 holding a cartridge 18 is contained within the housing 11.

The cartridge 18 comprises a pierceable septum 18a at its distal end, and contains liquid medicament which is to be delivered to a patient during injection. The cartridge 18 comprises a distal end portion which is shaped to be accommodated into a recess in the needle holder 25. A needle holder 25 is located near a distal end of the cartridge 18. The needle holder 25 holds a hollow injection needle 17 which, in an initial state, is not in contact with the pierceable septum 18a of the cartridge 18, as can be seen in FIG. 2A.

The cartridge 18 further comprises a piston, stopper or bung 23 for sealing the syringe 18 and displacing the liquid medicament through a hollow injection needle 17 when the injection needle 17 is pierced through the septum 18a at the distal end of the cartridge 18. The piston 23 is arranged to be push towards the distal end of the housing 11 by a plunger (not shown in the drawing) which is actuated by a button (such as button 22 shown in FIGS. 1A and 1B).

The needle holder 25 comprises a hollowed recess in the centre so as to accommodate the distal end portion of the cartridge 18. The needle holder 25 also comprises an engaging element 26 which is configured to lock the distal end portion of the cartridge 18 in place once it has fitted into the hollowed recess of the needle holder 25. The engaging element 26 in the present embodiment is a projection. The functionality of the engaging element 26 will be explained in further detail with respect to FIGS. 3 and 4.

An inner sleeve 13 is arranged within the housing 11, the inner sleeve 13 being configured to be retractable such that when the housing 11 is pushed against a surface (e.g. an injection site), the inner sleeve 13 retracts into the housing 11 against a spring force provided by a spring element (not shown in the drawing) in the housing 11. The inner sleeve 13 comprises a guide rib 29 which is configured to hold the cartridge holder 19 in place within the housing 11.

The injection device 30 further comprises a removable cap 12. A needle shield 24 is arranged within the removable cap 12. The hollow injection needle 17 is covered by the needle shield 27 arranged within the removable cap 12 when the removable cap 12 is engaged with the housing 11. The removable cap 12 comprises an inner cap portion which is configured to be fitted within the inner sleeve 13 when the removable cap 12 is attached to the housing 11.

A first rotary gear 27a and a second rotary gear 27b are respectively rotatably mounted at two opposite ends at a distal end of the cartridge holder 19. The first rotary gear 27a is rotatably mounted at a distal end of the cartridge holder 19 at one side while the second rotary gear 27b is rotatably mounted at the distal end of the cartridge holder 19 at a position circumferentially opposite to the first rotary gear 27a.

As will be explained in further detail below, the first rotary gear 27a and the second rotary gear 27b are part of a translating mechanism which engages the needle holder 25 with the removable cap 12 such that a linear distal movement of the removable cap 12 causes a linear proximal movement of the needle holder 25. In other words, the translating mechanism in this embodiment is a gear assembly comprising the first rotary gear 27a, the second rotary gear 27b, and a linear gear assembly 28 as described in the following.

A linear gear assembly 28 is formed on the inner cap portion of the removable cap 12 and the outer surface of the needle holder 25. Specifically, the linear gear assembly 28 comprises a first linear gear 28a (labelled in FIG. 3) which is formed on the inner surface of the inner cap portion of the removable cap 12, and a second linear gear 28b (labelled in FIG. 3) which is formed on the outer surface of the needle holder 25. The first linear gear 28a and the second linear gear 28b are in the form of rack gears. The first linear gear 28a is in the form of a plurality of teeth formed in an inner circumferential surface of the inner cap portion of the removable cap 12, and the second linear gear 28b is in the form of a plurality of teeth formed in a peripheral surface of the needle holder 25.

The first rotary gear 27a is a pinion gear rotatably mounted between the inner cap portion of the removable cap 12 and the needle holder 25 such that the teeth of the first rotary gear 27a mesh with both the teeth of the first linear gear 28a and the second linear gear 28b. The gear assembly is configured such that linear distal movement of the removable cap 12 in a first direction (i.e. away from the housing 11) rotates the first rotary gear 27a, thereby causing a proximal linear movement of the needle holder 25 in a second direction, the second direction being opposite to the first direction, i.e. into the housing 11.

Similarly, the second rotary gear 27b is also a pinion gear rotatably mounted between the inner cap portion of the removable cap 12 and the needle holder 25, on another side of the needle holder 25, such that the teeth of the first rotary gear 27a mesh with both the teeth of the first linear gear 28a and the second linear gear 28b. The gear assembly is configured such that linear distal movement of the removable cap 12 in a first direction (i.e. away from the housing 11) rotates the second rotary gear 27b together with the first rotary gear 27a, thereby causing a proximal linear movement of the needle holder 25 in a second direction, the second direction being opposite to the first direction, i.e. into the housing 11.

Figure 2B:
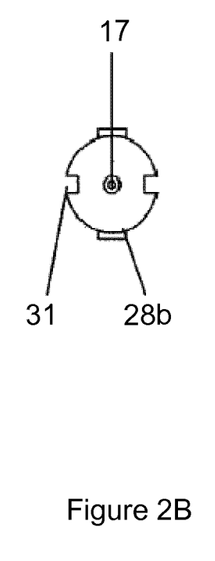
FIG. 2B is a schematic cross-sectional view of the needle holder of FIG. 2A in an axial view from the distal end.

FIG. 2B is a schematic cross-sectional view of the needle holder of FIG. 2A in an axial view from the distal end.

As seen in FIG. 2B, the needle holder 25 comprises a hollow injection needle 17 that is located in the centre of the needle holder, a guide groove 31 arranged at each side of the needle holder 24, and the second linear gear 28b. The guide groove 31 is arranged to ensure that only axial movement is allowed within the injection device 30. For example, the guide groove 31 in this embodiment is engaged with an engaging member (not shown in the drawings) at the housing 11 so as to limit rotational movement between the needle holder 25 and the housing 11.

Figure 3:
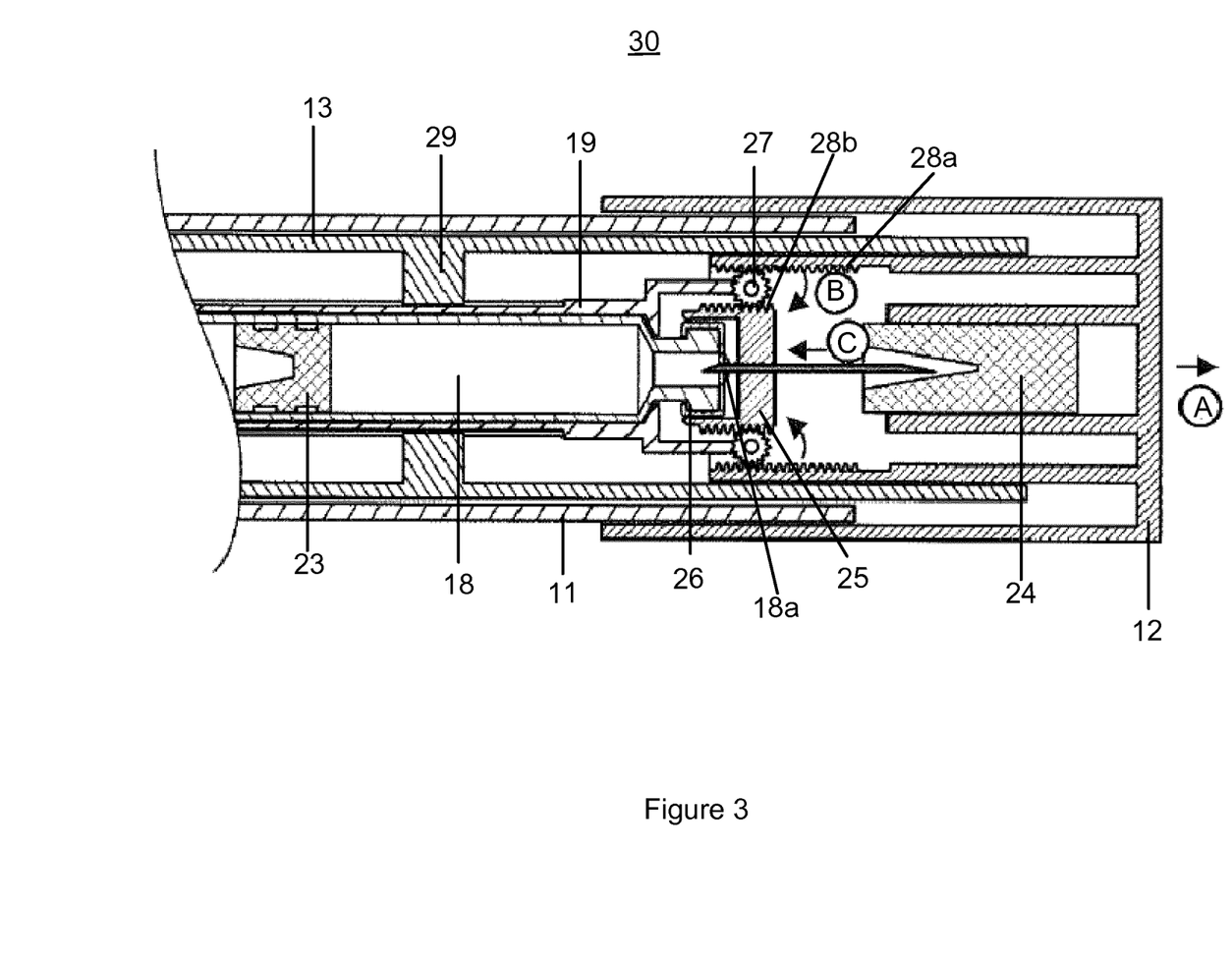
FIG. 3 is a schematic cross-sectional view of part of the injection device of the first embodiment in an intermediate state.

FIG. 3 is a schematic cross-sectional view of part of the injection device of the first embodiment in an intermediate state In the intermediate state, the removable cap 12 is in the process of being pulled away from the housing 11 in the direction indicated by arrow 'A'. This linear distal movement of the removable cap 12 means that the inner cap portion of the removable cap 12 is also moved linearly and distally with respect to the housing 11.

The first linear gear 28a arranged on the inner surface of the inner cap portion of the removable cap 12 is configured such that a linear distal movement of the removable cap 12 causes rotation of the first rotary gear 27a and second rotary gear 27b. In this embodiment, as viewed in FIG. 3, when the removable cap 12 moves linearly and distally in the first direction indicated by arrow 'A' (i.e. to the right), the first linear gear 28a meshes with the first rotary gear 27a to urge the first rotary gear 27a to rotate in a clockwise direction (indicated by arrow 'B') while the second rotary gear 27b is also urged by the first linear gear 28a at a circumferentially opposite position to rotate in an anti-clockwise direction.

The rotation of the first rotary gear 27a and the second rotary gear 27b in turn urges the second linear gear 28b to translate proximally towards the syringe 18 (i.e. towards the proximal end of the housing 11) in a direction indicated by arrow 'C'. The needle holder 25 therefore is translated towards the syringe 18 in the second direction, and the injection needle 17 included in the needle holder 25 pierces through the pierceable septum 18a located at the distal end of the syringe 18 in order to obtain access to medicament contained therein.

As shown in FIG. 3, the distal end portion of the cartridge 18 is not fully accommodated in the hollowed recess in the needle holder 25 in the intermediate state. A further translation movement of the needle holder 25 towards the proximal end of the housing 11 would be required for the distal end portion of the cartridge to be urged into the hollowed recess of the needle holder 25.

Figure 4:
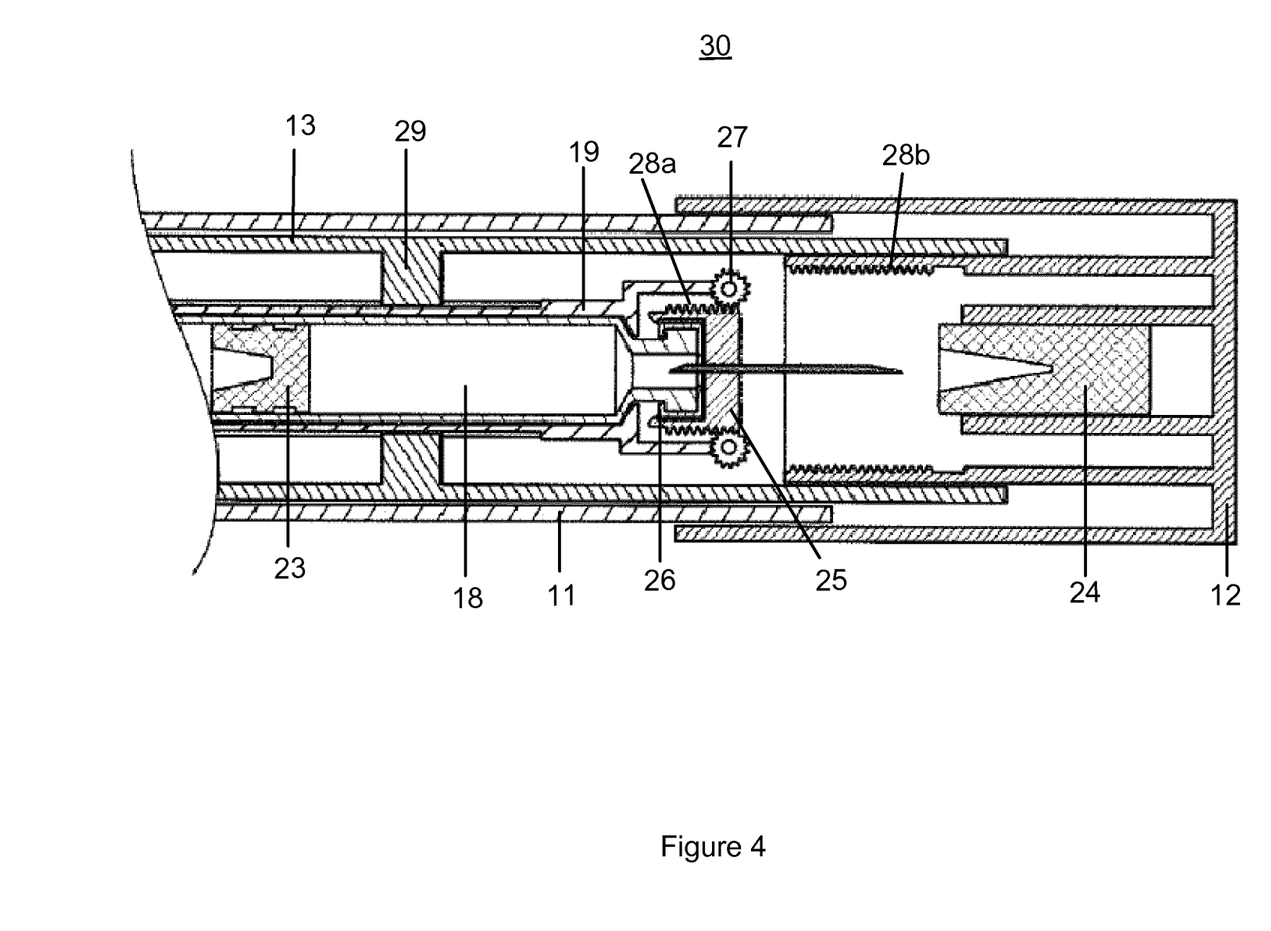
FIG. 4 is a schematic cross-sectional view of part of the injection device of the first embodiment in a final state.

FIG. 4 is a schematic cross-sectional view of part of the injection device of the first embodiment in a final state.

In the final state, the removable cap 12 is pulled further away from the rest of the injection device 30. The further linear movement of the removable cap 12 away from the housing 11 causes rotation of the first rotary gear 27a and second rotary gear 27b to continue. The first rotary gear 27a is urged to continue to rotate in a clockwise direction (indicated by arrow 'B') while the second rotary gear 27b is urged to continue to rotate in an anti-clockwise direction. This in turn urges the second linear gear 28b, and therefore the needle holder 25, to translate towards the syringe 18 further.

Once the distal end portion of the syringe 18 is fully accommodated into the hollowed recess in the needle holder 25, it is locked in place by the engaging element 26 of the needle holder. In this embodiment, specifically, the engaging element 26 serve as a clip so as to hold the distal end portion of the syringe 18 within the hollowed recess within the needle holder 25. Therefore, the needle holder 25 is secured together with the syringe 18 which ensures safety during injection.

Moreover, as the removable cap 12 is being pulled away from the injection device 30, the needle shield 24 at the removable cap 12 no longer covers the injection needle 17. Therefore, once the removable cap 12 is completely removed, the injection device 30 is ready for injection.

The arrangement as described above allows the cartridge and the needle assembly (i.e. needle holder and injection needle) to be quickly prepared for injection, simply by pulling the removable cap 12 away from the housing 11 of the injection device 30. This eliminates the need for the user to perform the assembly of the cartridge and the needle assembly manually and therefore prevents stick injuries and saves time.

A sequence of the operation of the auto-injector device 30 according to the first embodiment is described as follows:

A user pulls the removable cap 12 so as to disengage it from the housing 11. As the removable cap 12 is being pulled away from the housing 11, the linear movement of the first linear gear 27a at the inner cap portion urges the first rotary gear 27a to rotate in a clockwise direction (indicated by arrow 'B' in FIG. 3) while the second rotary gear 27b is urged to rotate in an anti-clockwise direction.

The rotation of the first rotary gear 27a and the second rotary gear 27b in turn urges the second linear gear 28b to translate towards the syringe 18 (i.e. towards the proximal end of the housing 11) in a direction indicated by arrow 'C' in FIG. 3. The needle holder 25 therefore is translated towards the syringe 18 in the second direction, and the injection needle 17 included in the needle holder 25 pierces through the pierceable septum 18a located at the distal end of the syringe 18 in order to obtain access to medicament contained therein.

As the removable cap 12 is continuously being pulled away from the housing 11, the further linear movement of the removable cap causes further rotation of the first rotary gear 27a and second rotary gear 27b. This in turn urges the second linear gear 28b, and therefore the needle holder 25, to translate towards the syringe 18 further. Once the distal end portion of the syringe 18 is fully accommodated into the hollowed recess in the needle holder 25, it is locked in place by the engaging element 26 of the needle holder 25 such that the connection between the syringe 18 and the needle holder 25 is now secure.

After the removable cap 12 has been completely disengaged from the housing 11, the injector device 30 is pressed against an injection site, e.g. a patient's skin. A user, e.g. the patient or a caregiver, grabs the auto-injector device 30 with their whole hand and pushes the distal end of the auto-injector device 30 against the injection site.

When pushed against the injection site, the inner sleeve 13 of the injector device 10 retracts into the housing 11 to expose the hollow injection needle 17. After the needle 17 has been inserted into the injection site, a driving mechanism is activated (e.g. pressing a button) so as to push the piston 23 towards the distal end of the housing 11 so as to displace medicament contained in the cartridge 18 through the injection needle 17.

In the embodiment as described above, before the distal end portion of the cartridge is fully accommodated into the hollowed recess of the needle holder, the distance moved by the removable cap away from the housing from the initials state is equal to the distance moved by the needle holder towards the cartridge. However, in alternative embodiments, the teeth of the first linear gear and the teeth of the second linear gear may be configured with different sizes so as to achieve different rack gains.

The rack gain of a rack and pinion mechanism is defined as a displacement of the rack gear for each turn of the pinion gear. By configuring the first and second linear gears such that the second linear gear has a greater rack gain than the first linear gear, the linear distance required for the removable cap to be pulled away from the housing in order for the needle holder to be translated towards and become secured with the cartridge is reduced. Therefore, a more efficient translating mechanism is achieved.

In alternative embodiments, the gear assembly may comprise a single rotary gear instead of a first and second rotary gears as described above.

In alternative embodiments, the gear assembly may comprise further rotary gears, in addition to the first and second rotary gears.

In alternative embodiments, the first linear gear and/or the second linear gear may adopt a helical thread arrangement instead of a rack gear arrangement.

In alternative embodiments, any of the first rotary gear, second rotary gear, first linear gear, and second linear gear may be arranged at a different position in the injection device.

In alternative embodiments, the removable cap may not comprise an inner cap portion. In these embodiments, the second linear gear may be arranged on the inner surface of the removable cap itself. Accordingly, the size of the first and second rotary gears may be adjusted such that it is suitably rotatably mounted between the first and second linear gears. Moreover, in these alternative embodiments, the removable cap may be made of elastic material such that the removable cap can be forced fitted into the housing.

In alternative embodiments, instead of a gear assembly having a first rotary gear, a second rotary gear, a first linear gear, and a second linear gear, the translating mechanism may comprise a pulley system including at least one pulley and a string. In these alternative embodiments, the at least one pulley may be mounted at the distal end of the cartridge holder, the string may be attached to the inner cap portion of the removable cap at one end and attached to the needle holder at an opposite end. The string may be made of specific material such that it can be broken with sufficient force. Therefore, when exerted with sufficient force, the string can be broken after the distal end portion is fully accommodated into the hollowed recess of the needle holder, such that the removable cap can be completely detached from the rest of the injection device.

Although claims have been formulated in this application to particular combinations of features, it should be understood that the scope of the disclosure also includes any novel features or any novel combinations of features disclosed herein either explicitly or implicitly or any generalization thereof, whether or not it relates to the same invention as presently claimed in any claim and whether or not it mitigates any or all of the same technical problems as does the present invention. The applicant hereby gives notice that new claims may be formulated to such features and/or combinations of features during the prosecution of the present application or of any further application derived therefrom.

Those skilled in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, and Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injection device comprising:
    a housing containing a cartridge;
    a needle holder including an injection needle;
    a cap that is removably engaged with the housing; and
    a translating mechanism comprising a gear assembly, the gear assembly comprising:
        a first rotary gear,
        a first linear gear, and
        a second linear gear,
    wherein the translating mechanism is configured such that linear distal movement of the cap causes proximal movement of the needle holder such that the injection needle pierces the cartridge.

2. The injection device of claim 1, wherein the cartridge comprises a pierceable septum, and wherein the injection needle is arranged to pierce the pierceable septum when the needle holder is urged against the cartridge.

3. The injection device of claim 1, further comprising a cartridge holder configured to contain the cartridge, and wherein the first rotary gear is rotatably mounted at a distal end of the cartridge holder between the needle holder and the removable cap, the first rotary gear being arranged to engage the first linear gear and the second linear gear.

4. The injection device of claim 1, wherein the first linear gear is arranged on an inner surface of the cap.

5. The injection device of claim 1, wherein the second linear gear is arranged on an outer surface of the needle holder.

6. The injection device of claim 1, further comprising a needle shield fixed to the cap, wherein the needle shield is configured to cover the needle when the cap is engaged with the housing.

7. The injection device according to claim 1, wherein the cartridge contains a medicament.

8. The injection device according to claim 1,
    wherein the injection device is an auto-injector.

9. The injection device of claim 3, further comprising a second rotary gear rotatably mounted at the distal end of the cartridge holder between the needle holder and the removable cap, at a position circumferentially opposite to the first rotary gear, wherein the second rotary gear is arranged to engage the first linear gear and the second linear gear.

10. The injection device of claim 5, wherein the cap further comprises an inner cap portion, wherein the first linear gear is positioned on an inner surface of the inner cap portion.

11. A method of coupling a cartridge and a needle holder including an injection needle within an injection device, the method comprising:
    converting distal movement of a removable cap into proximal movement of the needle holder via a translating mechanism, such that the injection needle pierces the cartridge.

12. The method of claim 11, wherein converting distal movement of the removable cap into proximal movement of the needle holder comprises engaging a first linear gear at the removable cap with a first rotary gear at the housing and causing the first rotary gear to engage a second linear gear at the needle holder such that the needle holder moves proximally towards the cartridge.

13. The method according to claim 11, further comprising piercing a pierceable septum of the cartridge with the injection needle.

14. The method according to claim 11, further comprising locking the needle holder in place by connecting an engagement element of the needle holder with the cartridge such that the cartridge and needle holder and translationally coupled.

15. The method according to claim 13, further comprising piercing the pierceable septum of the cartridge fluidly connects the injection needle with a substance within the cartridge.

16. The method according to claim 15, wherein the substance within the cartridge is medicament.

* * * * *